(12) United States Patent
Steffensmeier et al.

(10) Patent No.: US 7,641,661 B2
(45) Date of Patent: *Jan. 5, 2010

(54) ADJUSTABLE RESECTION GUIDE

(75) Inventors: Scott J. Steffensmeier, Warsaw, IN (US); Adam H. Sanford, Warsaw, IN (US)

(73) Assignee: Zimmer Technology, Inc., Warsaw, IN (US)

( * ) Notice: Subject to any disclaimer, the term of this patent is extended or adjusted under 35 U.S.C. 154(b) by 556 days.

This patent is subject to a terminal disclaimer.

(21) Appl. No.: 10/746,385

(22) Filed: Dec. 26, 2003

(65) Prior Publication Data

US 2005/0143746 A1    Jun. 30, 2005

(51) Int. Cl.
*A61B 17/58* (2006.01)
*A61F 2/00* (2006.01)

(52) U.S. Cl. .................................................... 606/88

(58) Field of Classification Search ............... 606/53, 606/86, 87, 88, 89, 90, 105
See application file for complete search history.

(56) References Cited

U.S. PATENT DOCUMENTS

| | | | |
|---|---|---|---|
| 2,697,433 A | 12/1954 | Zehnder | |
| 3,532,088 A | 10/1970 | Fiore | |
| 4,349,018 A | 9/1982 | Chambers | |
| 4,457,307 A | 7/1984 | Stillwell | |
| 4,524,766 A * | 6/1985 | Petersen | 606/88 |
| 4,566,448 A | 1/1986 | Rohr, Jr. | |
| 4,567,886 A | 2/1986 | Petersen | |
| 4,574,794 A | 3/1986 | Cooke et al. | |
| 4,646,729 A | 3/1987 | Kenna et al. | |
| 4,738,253 A | 4/1988 | Buechel et al. | |
| 4,759,350 A | 7/1988 | Dunn et al. | |
| 4,825,857 A | 5/1989 | Kenna | |
| 4,841,975 A * | 6/1989 | Woolson | 600/425 |
| 4,938,762 A | 7/1990 | Wehrli | |
| 4,952,213 A | 8/1990 | Bowman et al. | |
| 5,002,547 A | 3/1991 | Poggie et al. | |
| 5,007,936 A | 4/1991 | Woolson | |
| 5,116,338 A | 5/1992 | Walker | |
| 5,122,144 A | 6/1992 | Bert | |
| 5,213,112 A | 5/1993 | Niwa et al. | |
| 5,230,338 A | 7/1993 | Allen et al. | |
| 5,234,433 A | 8/1993 | Bert | |
| 5,251,127 A | 10/1993 | Raab | |
| 5,275,603 A | 1/1994 | Ferrante et al. | |
| 5,305,203 A | 4/1994 | Raab | |
| 5,306,276 A * | 4/1994 | Johnson et al. | 606/86 |
| 5,342,367 A | 8/1994 | Ferrante et al. | |
| 5,342,368 A | 8/1994 | Petersen | |

(Continued)

FOREIGN PATENT DOCUMENTS

| | | |
|---|---|---|
| DE | 20202615 U1 | 6/2002 |
| DE | 20303498 U1 | 7/2003 |
| EP | 0104732 A1 | 4/1984 |
| EP | FR2648699 A1 | 12/1990 |
| EP | 00709061 A1 | 5/1996 |

(Continued)

OTHER PUBLICATIONS

Zimmer, IM: The M/G™ Unicompartmental Knee Minimally Invasive Surgical Technique, 2002.

*Primary Examiner*—Anu Ramana
(74) *Attorney, Agent, or Firm*—Baker & Daniels LLP

(57) ABSTRACT

An adjustable resection guide is provided for guiding cutting of the tibia and/or femur during knee replacement surgery.

21 Claims, 6 Drawing Sheets

U.S. PATENT DOCUMENTS

| | | | |
|---|---|---|---|
| 5,344,423 A | 9/1994 | Dietz et al. | |
| 5,364,401 A | 11/1994 | Ferrante et al. | |
| 5,364,402 A | 11/1994 | Mumme et al. | |
| 5,368,552 A | 11/1994 | Williamson et al. | |
| 5,445,640 A * | 8/1995 | Johnson et al. | 606/86 |
| 5,451,228 A | 9/1995 | Johnson et al. | |
| 5,458,645 A | 10/1995 | Bertin | |
| 5,474,559 A | 12/1995 | Bertin et al. | |
| 5,484,446 A | 1/1996 | Burke et al. | |
| 5,486,180 A | 1/1996 | Dietz et al. | |
| 5,514,139 A | 5/1996 | Goldstein et al. | |
| 5,514,143 A | 5/1996 | Bonutti et al. | |
| 5,527,316 A | 6/1996 | Stone et al. | |
| 5,540,696 A | 7/1996 | Booth et al. | |
| 5,551,429 A | 9/1996 | Fitzpatrick et al. | |
| 5,562,674 A | 10/1996 | Stalcup et al. | |
| 5,593,411 A | 1/1997 | Stalcup et al. | |
| 5,597,379 A | 1/1997 | Haines et al. | |
| 5,601,563 A | 2/1997 | Burke et al. | |
| 5,611,802 A | 3/1997 | Samuelson et al. | |
| 5,628,750 A | 5/1997 | Whitlock et al. | |
| 5,643,272 A | 7/1997 | Haines | |
| 5,649,928 A | 7/1997 | Grundei | |
| 5,681,316 A | 10/1997 | DeOrio et al. | |
| 5,681,320 A | 10/1997 | McGuire | |
| 5,682,886 A | 11/1997 | Delp et al. | |
| 5,683,397 A | 11/1997 | Vendrely et al. | |
| 5,688,280 A | 11/1997 | Booth, Jr. | |
| 5,704,941 A | 1/1998 | Jacober et al. | |
| 5,743,915 A | 4/1998 | Bertin et al. | |
| 5,755,803 A | 5/1998 | Haines et al. | |
| 5,776,201 A | 7/1998 | Colleran et al. | |
| 5,788,700 A * | 8/1998 | Morawa et al. | 606/88 |
| 5,800,438 A | 9/1998 | Tuke et al. | |
| 5,810,827 A | 9/1998 | Haines et al. | |
| 5,824,085 A | 10/1998 | Sahay et al. | |
| 5,860,980 A | 1/1999 | Axelson et al. | |
| 5,871,018 A | 2/1999 | Delp et al. | |
| 5,879,354 A | 3/1999 | Haines et al. | |
| 5,904,691 A | 5/1999 | Barnett et al. | |
| 5,911,723 A | 6/1999 | Ashby et al. | |
| 5,921,992 A | 7/1999 | Costales et al. | |
| 5,995,738 A | 11/1999 | DiGioia, III et al. | |
| 6,002,859 A | 12/1999 | DiGioia, III et al. | |
| 6,033,415 A | 3/2000 | Mittelstadt et al. | |
| 6,051,016 A | 4/2000 | Mesaros et al. | |
| 6,056,754 A | 5/2000 | Haines et al. | |
| 6,077,270 A | 6/2000 | Katz | |
| 6,090,114 A * | 7/2000 | Matsuno et al. | 606/88 |
| 6,167,145 A | 12/2000 | Foley et al. | |
| 6,197,064 B1 | 3/2001 | Haines et al. | |
| 6,267,762 B1 | 7/2001 | Millard et al. | |
| 6,285,902 B1 | 9/2001 | Kienzle, III et al. | |
| 6,296,646 B1 | 10/2001 | Williamson | |
| 6,396,939 B1 | 5/2002 | Hu et al. | |
| 6,402,762 B2 | 6/2002 | Hunter et al. | |
| 6,430,434 B1 | 8/2002 | Mittelstadt | |
| 6,450,978 B1 | 9/2002 | Brosseau et al. | |
| 6,475,228 B1 | 11/2002 | Mesaros et al. | |
| 6,477,400 B1 | 11/2002 | Barrick | |
| 6,478,799 B1 | 11/2002 | Williamson | |
| 6,490,467 B1 | 12/2002 | Bucholz et al. | |
| 6,503,254 B2 | 1/2003 | Masini | |
| 6,514,259 B2 | 2/2003 | Picard et al. | |
| 6,551,325 B2 | 4/2003 | Neubauer et al. | |
| 6,554,837 B1 | 4/2003 | Hauri et al. | |
| 6,575,980 B1 | 6/2003 | Robie et al. | |
| 6,595,997 B2 | 7/2003 | Axelson, Jr. et al. | |
| 6,632,225 B2 | 10/2003 | Sanford et al. | |
| 6,685,711 B2 | 2/2004 | Axelson, Jr. et al. | |
| 6,695,848 B2 | 2/2004 | Haines | |
| 6,712,824 B2 | 3/2004 | Millard et al. | |
| 6,859,661 B2 | 2/2005 | Tuke | |
| 6,932,823 B2 | 8/2005 | Grimm et al. | |
| 7,029,477 B2 | 4/2006 | Grimm | |
| 7,094,241 B2 | 8/2006 | Hodorek et al. | |
| 7,201,755 B2 | 4/2007 | Faoro | |
| 7,235,080 B2 | 6/2007 | Hodorek | |
| 7,335,206 B2 | 2/2008 | Steffensmeier et al. | |
| 7,371,240 B2 * | 5/2008 | Pinczewski et al. | 606/88 |
| 2002/0068942 A1 | 6/2002 | Neubauer et al. | |
| 2002/0133160 A1 | 9/2002 | Axelson, Jr. et al. | |
| 2002/0133162 A1 | 9/2002 | Axelson, Jr. et al. | |
| 2002/0133163 A1 | 9/2002 | Axelson, Jr. et al. | |
| 2002/0133164 A1 | 9/2002 | Williamson | |
| 2002/0198530 A1 | 12/2002 | Sanford | |
| 2003/0069585 A1 | 4/2003 | Axelson, Jr. et al. | |
| 2003/0069591 A1 | 4/2003 | Carson et al. | |
| 2003/0100906 A1 | 5/2003 | Rosa et al. | |
| 2003/0216741 A1 | 11/2003 | Sanford | |
| 2003/0225413 A1 | 12/2003 | Sanford et al. | |
| 2003/0233149 A1 | 12/2003 | Hodorek | |
| 2004/0039396 A1 | 2/2004 | Couture et al. | |
| 2004/0102785 A1 | 5/2004 | Hodorek | |
| 2004/0122305 A1 | 6/2004 | Grimm et al. | |
| 2004/0152955 A1 | 8/2004 | McGinley et al. | |
| 2004/0153062 A1 | 8/2004 | McGinley et al. | |
| 2004/0249387 A1 | 12/2004 | Faoro | |
| 2005/0070910 A1 | 3/2005 | Keene | |
| 2005/0182415 A1 | 8/2005 | Steffensmeier et al. | |
| 2005/0203528 A1 | 9/2005 | Couture et al. | |
| 2005/0203541 A1 | 9/2005 | Steffensmeier et al. | |
| 2006/0030855 A1 | 2/2006 | Haines | |
| 2006/0036257 A1 | 2/2006 | Steffensmeier | |
| 2006/0149276 A1 | 7/2006 | Grimm | |
| 2006/0189998 A1 | 8/2006 | Rasmussen | |
| 2006/0195111 A1 | 8/2006 | Couture | |
| 2006/0217734 A1 | 9/2006 | Sanford et al. | |
| 2006/0247647 A1 | 11/2006 | Hodorek et al. | |
| 2007/0173854 A1 | 7/2007 | Berger | |

FOREIGN PATENT DOCUMENTS

| | | | |
|---|---|---|---|
| EP | 0839501 B1 | 5/1998 | |
| EP | 00809969 B1 | 10/2002 | |
| EP | 1424042 B1 | 6/2004 | |
| EP | 1579812 A1 | 9/2005 | |
| FR | 2679766 A2 | 2/1993 | |
| FR | 2776176 A1 | 9/1999 | |
| FR | 2819168 A1 | 7/2002 | |
| WO | WO01/66021 A1 | 9/2001 | |
| WO | WO01/85038 A1 | 11/2001 | |
| WO | WO2004/017842 A2 | 3/2004 | |
| WO | WO2004/019792 A1 | 3/2004 | |

* cited by examiner

ADJUSTABLE RESECTION GUIDE

BACKGROUND

The invention relates to resection guides for guiding a cutter to cut a bone to receive a knee prosthesis. More particularly, the invention relates to adjustable resection guides.

Degenerative and traumatic damage to the articular cartilage of the knee joint can result in pain and restricted motion. Prosthetic joint replacement is frequently utilized to alleviate the pain and restore joint function. In this procedure, the damaged compartments of the joint are cut away and replaced with prosthetic components. Typically a resection guide is used to guide a cutter such as a saw blade or bur to cut a desired portion of the bone.

SUMMARY

The present invention provides a resection guide for guiding cutting of the tibia and/or femur during knee replacement surgery.

In one aspect of the invention, an adjustable resection guide includes an elongated base member, a tibial cut guide, and mediolateral and proximal-distal adjustment mechanisms. The tibial cut guide has a guide surface for guiding a cutter to cut the tibia. The mediolateral and proximal-distal adjustment mechanisms are interposed between the base member and tibial cut guide to permit the tibial cut guide to be positioned at a desired location adjacent the proximal tibia.

In another aspect of the invention, an adjustable resection guide includes a tibial cut guide having means for guiding a cutter to cut the tibia and a femoral cut guide having means for guiding a cutter to cut the femur. The femoral cut guide is mounted on the tibial cut guide in relative mediolateral translating relationship.

In another aspect of the invention, an adjustable resection guide includes a base member and a tibial cut guide mounted on the base member in relative proximal-distal translating relationship. A first proximal-distal adjustment mechanism is for making coarse adjustments in the relative proximal-distal position of the tibial cut guide relative to the base member and a second proximal-distal adjustment mechanism is for making fine adjustments in the relative proximal-distal position of the tibial cut guide relative to the base member.

In another aspect of the invention, an adjustable resection guide includes an elongated base member, a rod, a support member, and tibial cut guide. The base member includes an axial bore opening axially outwardly at its proximal end. The rod has a dovetail engagement formed on its proximal end and its distal end is received in the base member axial bore for axial translation. The support member has an outwardly opening radial slot and an axial bore communicating with the radial slot. The support member has a dovetail engagement formed on its distal end that engages the dovetail engagement of the rod for mediolateral translation. The tibial cut guide has a guide surface for guiding a cutter to cut the tibia and a support arm extending distally from the tibial cut guide. The support arm is received by the axial bore of the support member for axial translation. A portion of the support arm is threaded and engages a nut positioned within the radial slot of the support member such that rotating the nut causes the tibial cut guide to translate proximal-distally.

In another aspect of the invention, a method for guiding a cutter to cut bone adjacent a knee joint includes providing a resection guide comprising a tibial cut guide having means for guiding a cutter to cut the tibia and a femoral cut guide mountable on the tibial cut guide, the femoral cut guide comprising an outwardly projecting paddle and means for guiding a cutter to cut the femur, positioning the resection guide adjacent the tibia, mounting the femoral cut guide on the tibial cut guide, inserting the paddle into the joint space between the tibia and femur, and adjusting the proximal-distal position of the tibial and femoral resection guides together until the paddle abuts the femoral condyle.

In another aspect of the invention, a method for guiding a cutter to cut bone adjacent a knee joint includes providing a resection guide comprising an elongated base member having a longitudinal axis, the base member having a proximal end and a distal end, the base member being positionable adjacent the tibia with the longitudinal axis parallel to the tibial axis, a tibial cut guide having means for guiding a cutter to cut the tibia, and a stylus mountable on the tibial cut guide, the stylus having a reference surface for engaging the articulating end of the tibia, the tibial cut guide being mounted on the base member with a mediolateral adjustment mechanism interposed between the base member and the tibial cut guide, the mediolateral adjustment mechanism operable to adjust the tibial cut guide mediolaterally relative to the base member, and a proximal-distal adjustment mechanism interposed between the base member and the tibial cut guide, the proximal-distal adjustment mechanism operable to adjust the tibial cut guide proximal-distally relative to the base member, the proximal-distal adjustment mechanism comprising separate coarse adjustment and fine adjustment mechanisms, positioning the base member adjacent the tibia, mounting the stylus on the tibial cut guide, inserting the stylus into the joint space between the tibia and femur, adjusting the proximal-distal position of the tibial cut guide using the coarse and fine adjustment mechanisms until the stylus reference surface abuts the proximal tibial surface, and adjusting the mediolateral position of the tibial cut guide relative to the base to position the tibial cut guide in a desired mediolateral position.

In another aspect of the invention, a method for guiding a cutter to cut bone adjacent a knee joint includes providing a resection guide comprising a tibial cut guide having means for guiding a cutter to cut the tibia, a femoral cut guide mounted on the tibial cut guide in relative mediolateral translating relationship, the femoral cut guide comprising means for guiding a cutter to cut the femur, positioning the resection guide adjacent the tibia, translating the tibial cut guide mediolaterally to a desired mediolateral position relative to the tibia, and translating the femoral cut guide mediolaterally relative to the tibial cut guide to a desired mediolateral position relative to the femur.

BRIEF DESCRIPTION OF THE DRAWINGS

Various embodiments of the present invention will be discussed with reference to the appended drawings. These drawings depict only illustrative embodiments of the invention and are not to be considered limiting of its scope.

DESCRIPTION OF THE ILLUSTRATED EMBODIMENTS

Figure 1:
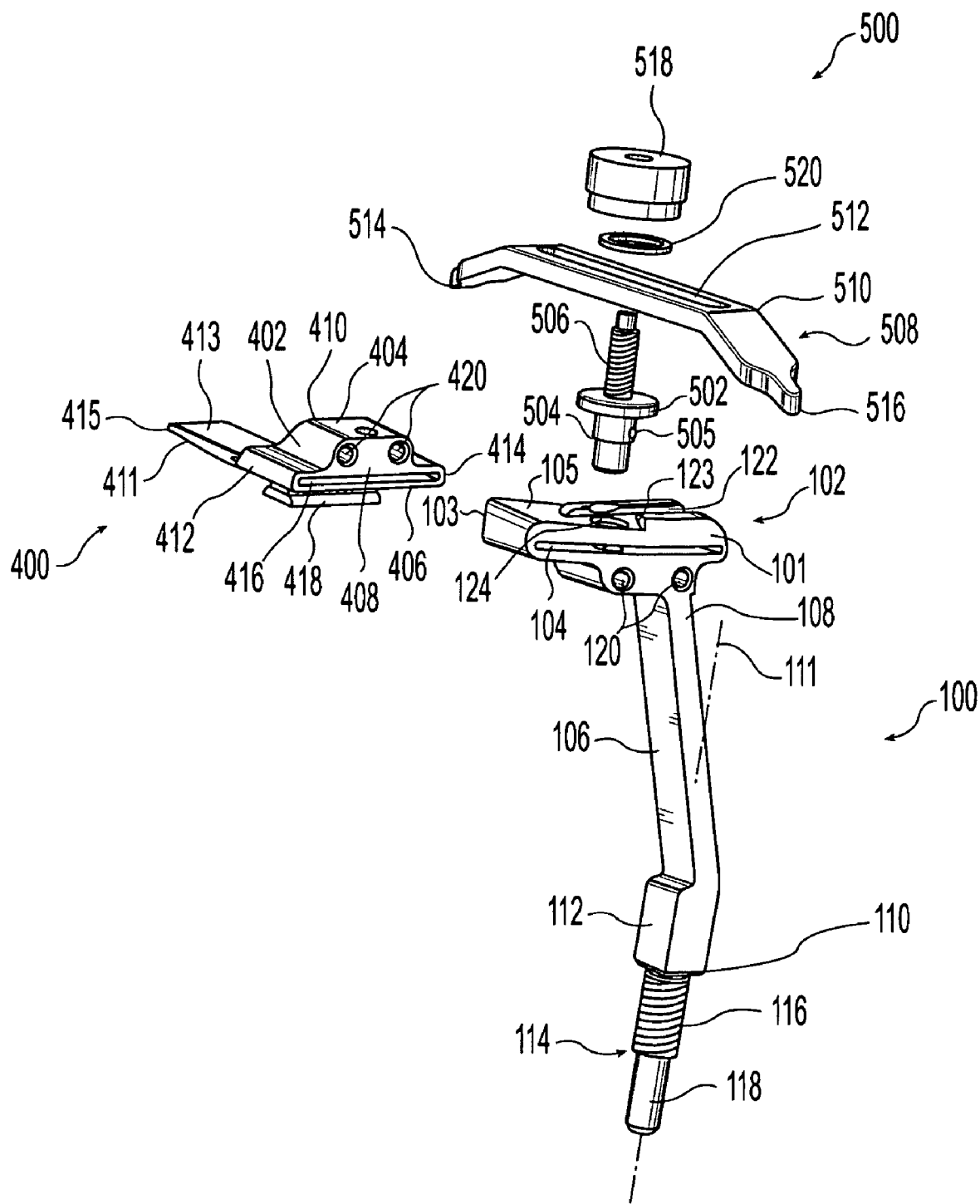
FIGS. 1-3 are exploded perspective views of an illustrative adjustable resection guide according to the present invention.

FIGS. 1-6 depict an illustrative adjustable resection guide 10 having a tibial cut guide 100, a support assembly 200, and an ankle clamp assembly 300 that interconnect to permit a variety of adjustments in the size and position of the resection guide 10. An optional modular femoral cut guide 400 and tibial depth setting stylus 500 are also shown. The use of the femoral cut guide 400 and stylus 500 with the adjustable resection guide 10 will be discussed after the basic form and function of the resection guide 10 has been fully described. Throughout this description the term proximal will be used to refer to locations nearer the hip joint and distal will be used to refer to locations further from the hip joint. Thus the inferior most portion of the femur in extension is the femoral condyle and the superior most portion of the tibia is the proximal tibial surface. Likewise, upper portions of the instruments as they would be mounted on the tibia are referred to as proximal and lower portions are referred to as distal.

Figure 4:
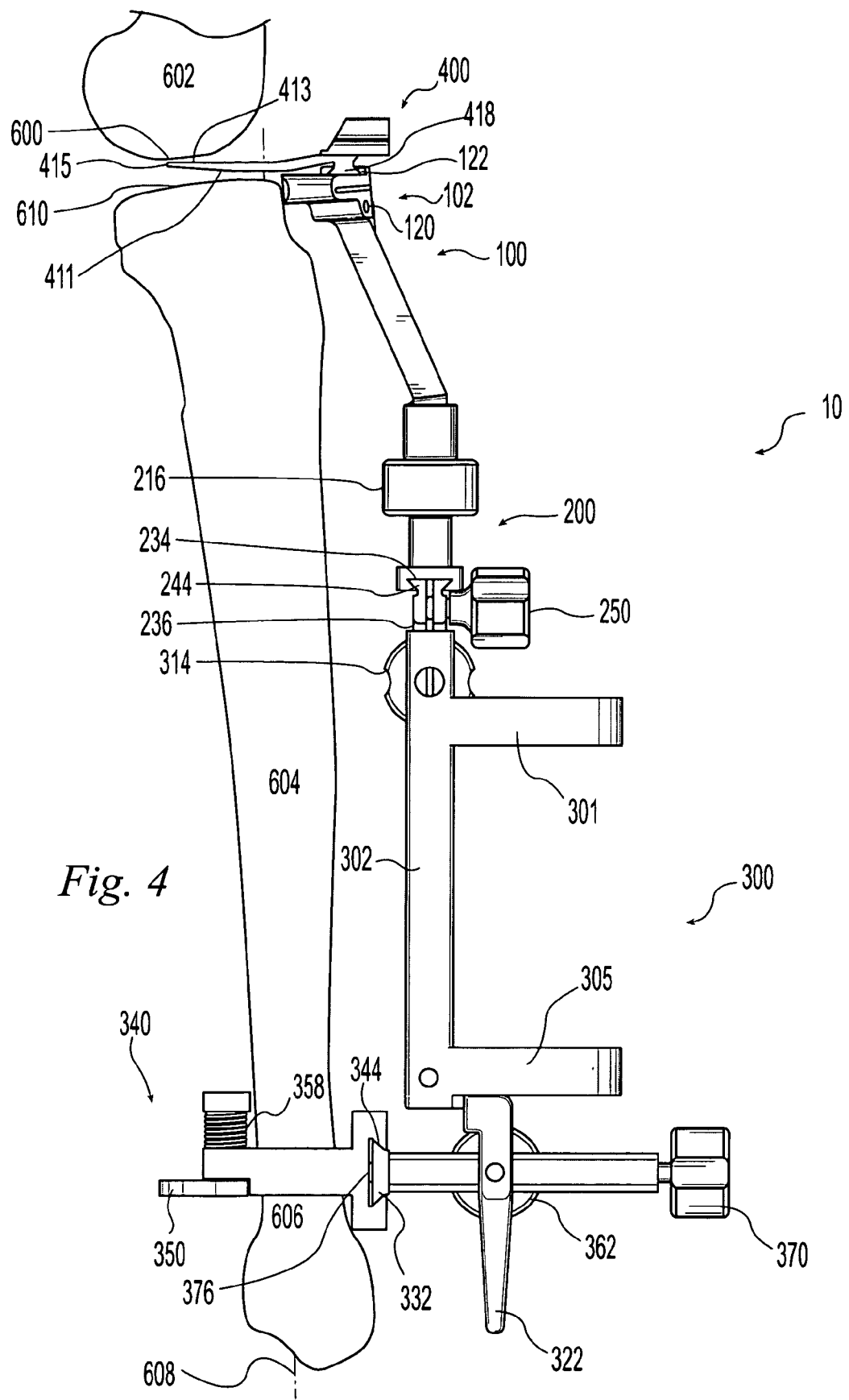
FIG. 4 is a side plan view of the resection guide of FIGS. 1-3 assembled with an optional illustrative femoral cut guide and positioned on a bone.

In FIG. 4, the resection guide 10 is depicted in use cutting the distal femur and proximal tibia with the knee in extension. However, the resection guide 10 may also be used to cut the knee in other degrees of flexion such as 90°, 45° and other suitable angles. Also, the resection guide 10 may be used to make other femoral cuts such as the posterior femoral cut, chamfer cuts, and other suitable cuts.

The tibial cut guide 100 (FIG. 1) includes a head 102 having an anterior aspect 101, a posterior aspect 103, and a proximal aspect 105. The head 102 includes a guide surface in the form of a cut slot 104 extending through the head from the anterior aspect 101 to the posterior aspect 103 for guiding a blade to cut the tibia. The guide surface may take other forms including open planar surfaces, line contact bearing surfaces, and other suitable guide surfaces. A support arm 106 extends distally from the head 102 from a proximal end 108 adjacent the head 102 to a distal end 110 spaced from the head 102. The head 102 and support arm 106 may be formed separately or as an integral piece as shown in the illustrative embodiment. The distal end 110 of the support arm is aligned along a vertical axis 111 and includes a bearing portion 112 having a non-circular cross section that connects to the support assembly 200 (FIG. 2). The non-circular cross section prevents rotation of the tibial cut guide 100 relative to the support assembly while permitting axial translation for height adjustment. The distal end 110 of the support arm further includes a mounting post 114 having a proximal threaded proximal portion 116 and a distal smooth portion 118. The threaded portion 116 is received by the support assembly 200 (FIG. 2) to provide fine control for adjusting the height of the tibial cut guide 100 relative to the support assembly 200. The smooth portion 118 is received by the support assembly 200 to provide increased side-to-side stability to the tibial cut guide 100 on the support assembly 200. The proximal end 108 of the support arm 106 is offset posteriorly relative to the distal end 110 so that the head 102 is offset posteriorly.

The tibial cut guide 100 includes one or more fixation holes 120 for receiving pins, screws, or other suitable fixation members to anchor the tibial cut guide 100 to the tibia prior to cutting the tibia. The fixation holes 120 may be provided at any suitable location on the tibial cut guide 100 as long as they anchor the tibial cut guide 100 securely. In the illustrative embodiment, the fixation holes 120 are located just below the cut slot 104 and extend through the head 102 from the anterior aspect 101 to the posterior aspect 103. The forces tending to move the cut guide 100 in use are caused by pressure from a cutter against the edges of the cut slot 104. Placement of the fixation holes 120 close to the cut slot 104 minimizes the moment arm over which the forces act and thus provides maximum stability. Placement of the fixation holes 120 close to the cut slot 104 also reduces the overall incision length required to resect the tibia as it permits fixation members to be placed in the same incision through which the bone resection takes place. This is especially useful in a minimally invasive surgical approach since it avoids having to lengthen the incision or create separate percutaneous punctures.

The tibial cut guide 100 further includes a femoral cut guide engagement portion in the form of a dovetail slot 122 formed mediolaterally on the proximal aspect 105 of the head 102 to receive dovetail rails from the femoral cut guide 400 in medial/lateral sliding arrangement. A portion 123 of the anterior side of the dovetail slot is relieved to ease attachment and detachment of the cut guide 400 as will be discussed more fully below. Although the illustrative embodiment has depicted the head 102 with a dovetail slot 122, the slot and rail arrangement may be reversed or a different attachment mechanism may be provided for connecting the optional femoral cut guide 400. The tibial cut guide 100 further includes a depth stylus engagement portion in the form of an axial bore 124 formed in the proximal aspect 105 of the head 102 for receiving a mounting post 504 on the tibial depth setting stylus 500. Although the illustrative embodiment has depicted an axial bore 124 in the head 102, the bore and post arrangement may be reversed or a different attachment mechanism may be provided for connecting the optional stylus 500.

The support assembly 200 (FIG. 2) includes a resection guide base 202 having a proximal end 204, a distal end 206 and an axis 208 therebetween. A non-circular bore 210 and a round bore 212 are aligned along the axis 208 to receive the distal end 110 of the support arm of the tibial cut guide 100. A slot 214 is positioned axially between the bores 210, 212 to receive a fine height adjustment knob 216 having an axial threaded bore 218. The knob 216 is free to rotate about the axis 208 within the slot 214 but is prevented from moving up and down along the axis by impingement with the top 220 and bottom 222 of the slot 214. The non-circular bore 210 of the resection guide base 202 receives the non-circular bearing portion 112 of the tibial cut guide 100 in axial sliding arrangement. The threaded bore 218 of the knob 216 receives the threaded portion 116 of the mounting post 114 of the tibial cut guide 100 for positive height control of the tibial cut guide 100 relative to the resection guide base 202. The round bore 212 receives the smooth portion 118 of the mounting post 114 of the tibial cut guide 100 for increased side-to-side stability of the tibial cut guide 100. When assembled (FIG. 5), the side of the knob 216 extends from the slot 214 to permit rotation of the knob 216 by thumb pressure from a user to move the tibial cut guide 100 axially up-and-down relative to the resection guide base 202.

Figure 5:
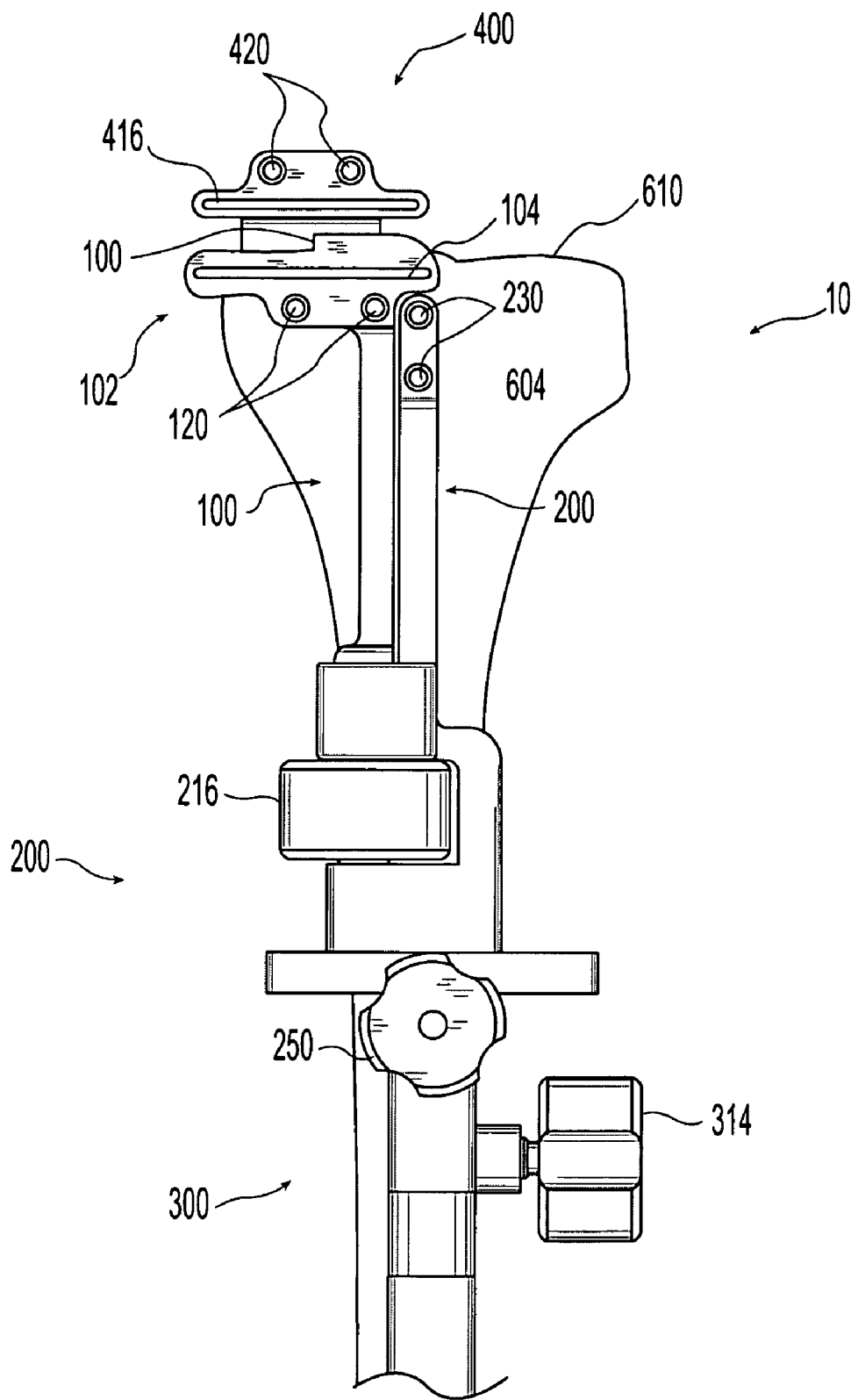
FIG. 5 is a front plan view of the upper portion of the assembled resection guide of FIG. 4 and positioned on a bone.

A fixation arm 226 projects upwardly from the proximal end 204 of the resection guide base 202 to a terminal end 228. The terminal end 228 is offset posteriorly such that the fixation arm 226 lies beside the support arm 106 of the tibial cut guide 100 and the terminal end 228 lies beside the head 102 of the tibial cut guide 100 when they are assembled (FIG. 5). The terminal end 228 includes one or more fixation holes 230 to receive fixation members for securing the resection guide base 202 to the tibia.

Figure 3:
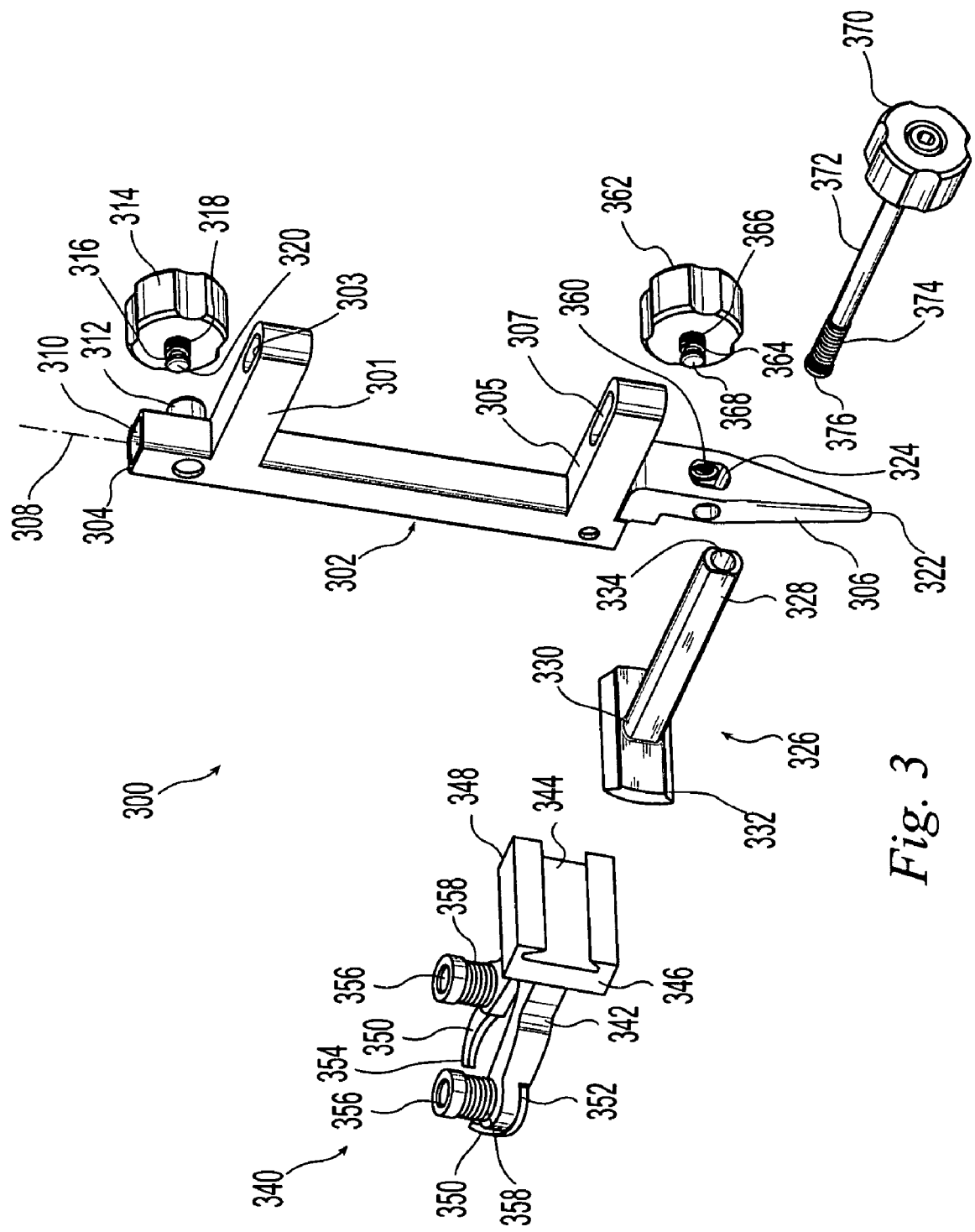

An elongated platform 232 is attached to the resection guide base 202 at its distal end 206. The platform 232 extends mediolaterally and includes a sliding attachment portion in the form of a mediolaterally extending dovetail slot 234 for receiving a distal extension rod 236. The distal extension rod 236 includes an elongated non-circular shaft 237 for connecting the resection guide base 202 to the ankle clamp assembly (FIG. 3). The extension rod 236 includes a proximal end 238, a distal end 240, and a longitudinal axis 242 extending therebetween. Dovetail rails 244 are formed at the proximal end 238 and are received by the dovetail slot 234 of the resection guide base 202 to permit mediolateral relative translation between the extension rod 236 and the resection guide base 202. A slot 246 extends from the proximal end 238 of the extension rod 236 distally to divide the dovetail rails 244 into two separate leaves 245 to provide a locking mechanism for fixing the relative position of the extension rod 236 and the resection guide base 202. One of the leaves 245 includes a threaded through bore 248 for receiving a locking knob 250. The locking knob 250 includes a shaft 252 having a threaded portion 254 and an end 256. The locking knob 250 is threaded into the threaded bore 248 of one of the leaves 245 until the end 256 of the shaft 252 contacts the opposite leaf 245. Further tightening of the locking knob 250 causes the leaves 245 to separate such that the dovetail rails 244 expand and grip the dovetail slot 234 to lock the relative position of the extension rod 236 and resection guide base 202. The illustrative embodiment has been shown with a dovetail slot 234 on the resection guide base 202 and dovetail rails 244 on the extension rod 236. However, the slot and rail arrangement may be reversed and/or other suitable connections may be provided to permit mediolateral adjustability.

The ankle clamp assembly 300 (FIG. 3) includes an ankle clamp base 302 having a proximal end 304, a distal end 306, and an axis 308 extending between the proximal and distal ends 304, 306. An axial non-circular bore 310 extends distally from the proximal end 304 to receive the distal extension rod 236 for axial translation. The non-circular shape of the bore 310 and extension rod 236 prevent the extension rod 236 from rotating relative to the ankle clamp base 302. Other shapes and mechanisms may also be used to prevent relative rotation of these parts. A boss 312 extends from the ankle clamp base 302 normal to the axis 308 near the proximal end 304. The boss 312 includes a threaded through bore communicating with the axial non-circular bore 310. A vertical, or proximal-distal, coarse adjustment locking knob 314 includes a shaft 316 having a threaded portion 318 and an end 320. The locking knob 314 is threaded into the boss 312 until the end 320 of the shaft 316 lightly contacts the extension rod 236 of the support assembly 200. Further tightening of the locking knob 314 against the extension rod 236 locks the vertical position of the extension rod 236 relative to the ankle clamp assembly 300.

A proximal extension arm 301 extends anteriorly from the ankle clamp base 302 and includes a proximal alignment rod hole 303. A distal extension arm 305 extends anteriorly from the ankle clamp base 302 and includes a distal alignment rod hole 307. An alignment rod (not shown) may optionally be positioned in the alignment rod holes 303, 307 to help visualize proper leg positioning such as alignment of the tibial axis with the center of the femoral head.

The distal end 306 of the ankle clamp base 302 is shaped into a distally directed pointer 322 to aid in aligning the ankle clamp assembly axis 308 with the center of a patients ankle. An anteroposterior through bore 324 in the distal end 306 receives an ankle clamp mounting post 326 for anteroposterior adjustment of the distal end 306. The bore 324 is keyed, for example with flat sides as shown, to prevent rotation of the mounting post 326 within the bore 324. The mounting post 326 includes a shaft having a cross sectional shape corresponding to the bore 324 and extending from an anterior end 328 to a posterior end 330. A mediolateral extending dovetail rail 332 is attached to the posterior end 330 of the mounting post 326. A threaded bore 334 extends through the mounting post 326 from the anterior end 328 to the posterior end 330 and on through the dovetail rail 332. An ankle clamp 340 includes a base 342 having a dovetail slot 344 extending between opposite sides 346, 348 of the base 342 for receiving the dovetail rail 332 of the mounting post 326 to permit mediolateral translation of the ankle clamp relative to the mounting post 326. A curved arm 350 having an attachment end 352 and a gripping end 354 attaches to each end 346, 348 of the clamp base 342 with a pivot pin 356. A coil spring 358 biases each arm 350 inwardly toward the other. With the mounting post 326 received within the bore 324 of the ankle clamp base 302, the ankle clamp 340 may be translated anteriorly and posteriorly by sliding the mounting post 326 in the bore 324. A threaded through bore 360 in the distal end 306 of the ankle clamp base 302 communicates with the bore 324 and receives an anterior/posterior (A/P) locking knob 362. The A/P locking knob 362 includes a shaft 364 having a threaded portion 366 and an end 368. The locking knob 362 is threaded into the threaded bore 360 until the end 368 of the shaft 364 lightly contacts the mounting post 326. Further tightening of the locking knob 362 against the mounting post 326 locks the A/P position of the mounting post 326 relative to the ankle clamp base 302. With the ankle clamp 340 assembled to the mounting post 326, the ankle clamp 340 may be translated mediolaterally by sliding the dovetail slot 344 over the dovetail rail 332. The threaded bore 334 of the mounting post 326 receives a medial/lateral (ML) locking knob 370. The M/L locking knob 370 includes a shaft 372 having a threaded portion 374 and an end 376. The locking knob 370 is threaded into the threaded bore 334 until the end 376 of the shaft 372 lightly contacts the dovetail slot 344 of the ankle clamp 340. Further tightening of the locking knob 370 against the dovetail slot 344 locks the M/L position of the ankle clamp 340 relative to the ankle clamp base 302.

Figure 2:
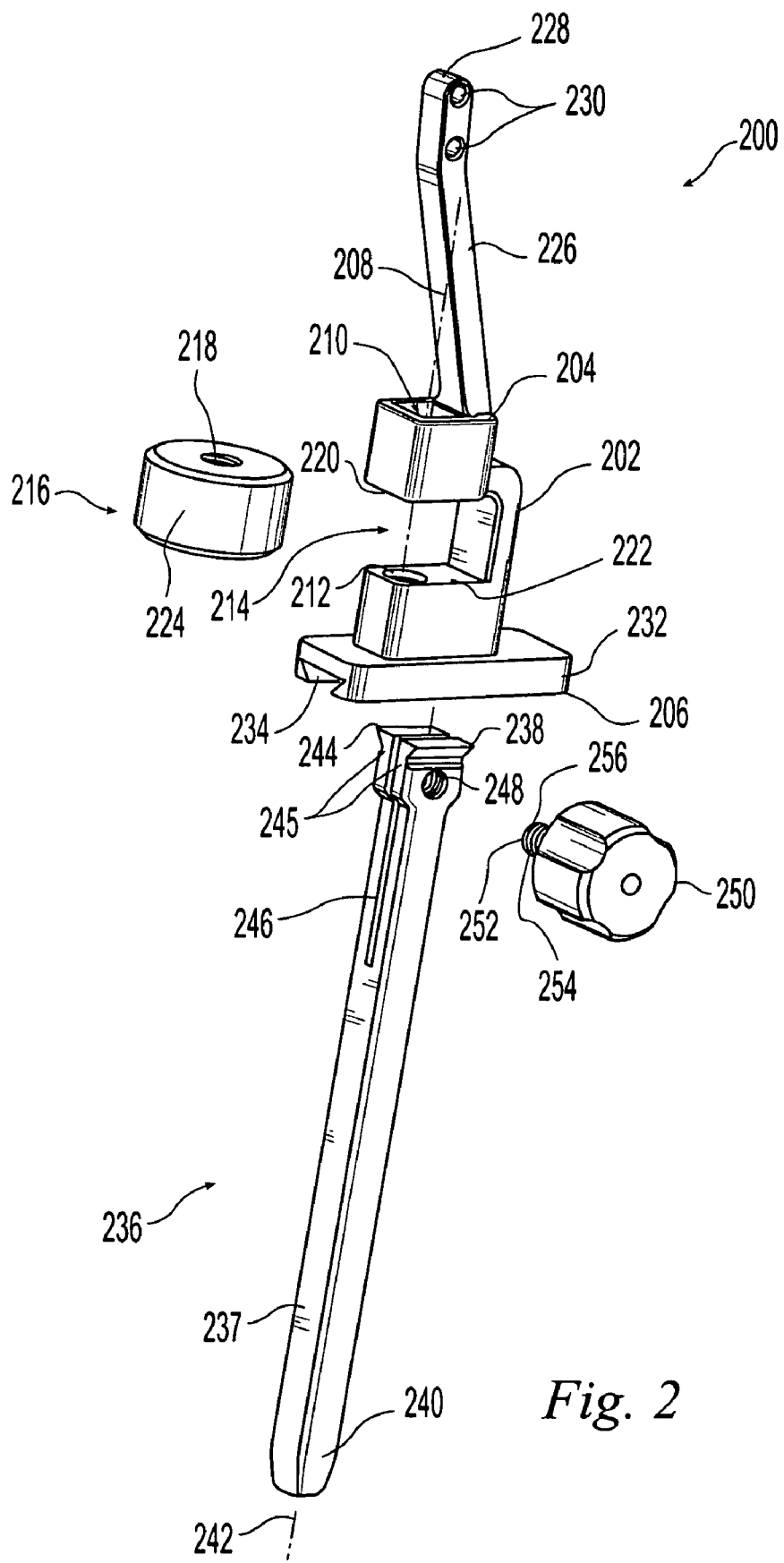

An illustrative optional modular femoral cut guide 400 is depicted in FIGS. 1, 4, and 5. The cut guide 400 includes a body 402 having a proximal aspect 404, a distal aspect 406, an anterior aspect 408, a posterior aspect 410, and sides 412, 414. The cut guide 400 includes a guide surface in the form of a cut slot 416 extending through the cut guide 400 from the anterior aspect 408 to the posterior aspect 410 between the sides 412, 414 for guiding a blade to cut the femur. The guide surface may take other forms including open planar surfaces, line contact bearing surfaces, and other suitable guide surfaces. A femoral reference paddle 411 extends from the posterior aspect 410 of the body 402 at a predetermined spacing distally of the cut slot 416. The paddle 411 includes a top surface 413 that may be abutted against the femoral condyle to position the cut slot 416 to remove a predetermined amount of bone from the femoral condyle or alternatively to space the tibial cut slot 104 a predetermined distance from the femoral condyle. The paddle 411 tapers posteriorly to a thin tip 415 to facilitate insertion into the joint space between the tibia and femur. The paddle 411 may be permanently attached (as shown) or modular (not shown). A modular paddle 411 may be provided to ease assembly and insertion of the adjustable resection guide 10 into the surgical wound. A modular paddle 411 also may be removed after the cut depth is set to permit the knee to be flexed while the cut guide 400 remains in place. A modular paddle 411 also permits omitting the paddle 411 in cases where the cut depth is set in another manner such as by referencing the tibia. A permanently attached paddle 411 may be formed as an integral part of the cut guide 400, welded to the cut guide, or attached in another suitable way. A modular paddle 411 may be bolted onto the cut guide 400, snapped in, carried in a slot, or otherwise attached to the cut guide 400. For example, one or more additional slots may be provided at a predetermined spacing distal to the cut slot 416 and extending from the anterior aspect to the posterior aspect. The paddle 411 may be inserted through the second slot from the anterior aspect 408 to the posterior aspect 410.

An attachment member in the form of a dovetail rail 418 projects from the distal aspect 406 of the cut guide 400 and extends mediolaterally along the distal aspect 406. The dovetail rail 418 is received by the dovetail slot 122 of the tibial cut guide head 102 for mediolateral translation of the femoral cut guide 400 relative to the tibial cut guide 100. The dovetail engagement maintains the angle and spacing between the cutting guide surfaces of the femoral and tibial cut guides 400, 100 constant while permitting mediolateral translation. The dovetail rail 418 extends mediolaterally a distance less than the distance between the sides 412, 414 of the femoral cut guide 400 and the dovetail slot 122 extends only part way across the proximal aspect of the tibial cut guide head 102 to facilitate mounting the femoral cut guide 400 on the tibial cut guide 100 without requiring extreme relative mediolateral positioning of the cut guides 100, 400. The relieved portion 123 of the dovetail slot 122 further facilitates mounting the femoral cut guide 400. To mount the femoral cut guide 400 on the tibial cut guide 100, the dovetail rail 418 is positioned to just clear the side of the dovetail slot 122 adjacent the relieved portion 123. In this position the mediolateral width of the positioned cut guides 100, 400 is much less than the combined widths of the individual cut guides 100, 400 and much less than would be the width of the positioned cut guides 100, 400 if the dovetail rail and slot 418, 122 extended across the full width of the cut guides 400, 100 and/or if the relieved portion 123 was not provided. This arrangement permits the femoral cut guide 400 to be mounted on the tibial cut guide 100 within the confines of a narrow incision such as the incision used in a minimally invasive approach to knee surgery. The femoral cut guide 400 is translated posteriorly until the dovetail rail 418 engages the dovetail slot 122 opposite the relieved portion 123. The femoral cut guide 400 is translated mediolaterally to engage the dovetail slot 122 adjacent the relieved portion 123. As described relative to the dovetail slot 122, the dovetail members may be reversed or other attachment mechanisms may be used. With the femoral cut guide 400 attached to the tibial cut guide 100, the femoral and tibial cut slots 416, 104 are positioned to guide cutters to remove a portion of the femur and tibia to create a predetermined gap for receiving an implant. Fixation holes 420 receive pins, screws, or other fixation members to attach the femoral cut guide at a desired location on the femur.

Figure 6:
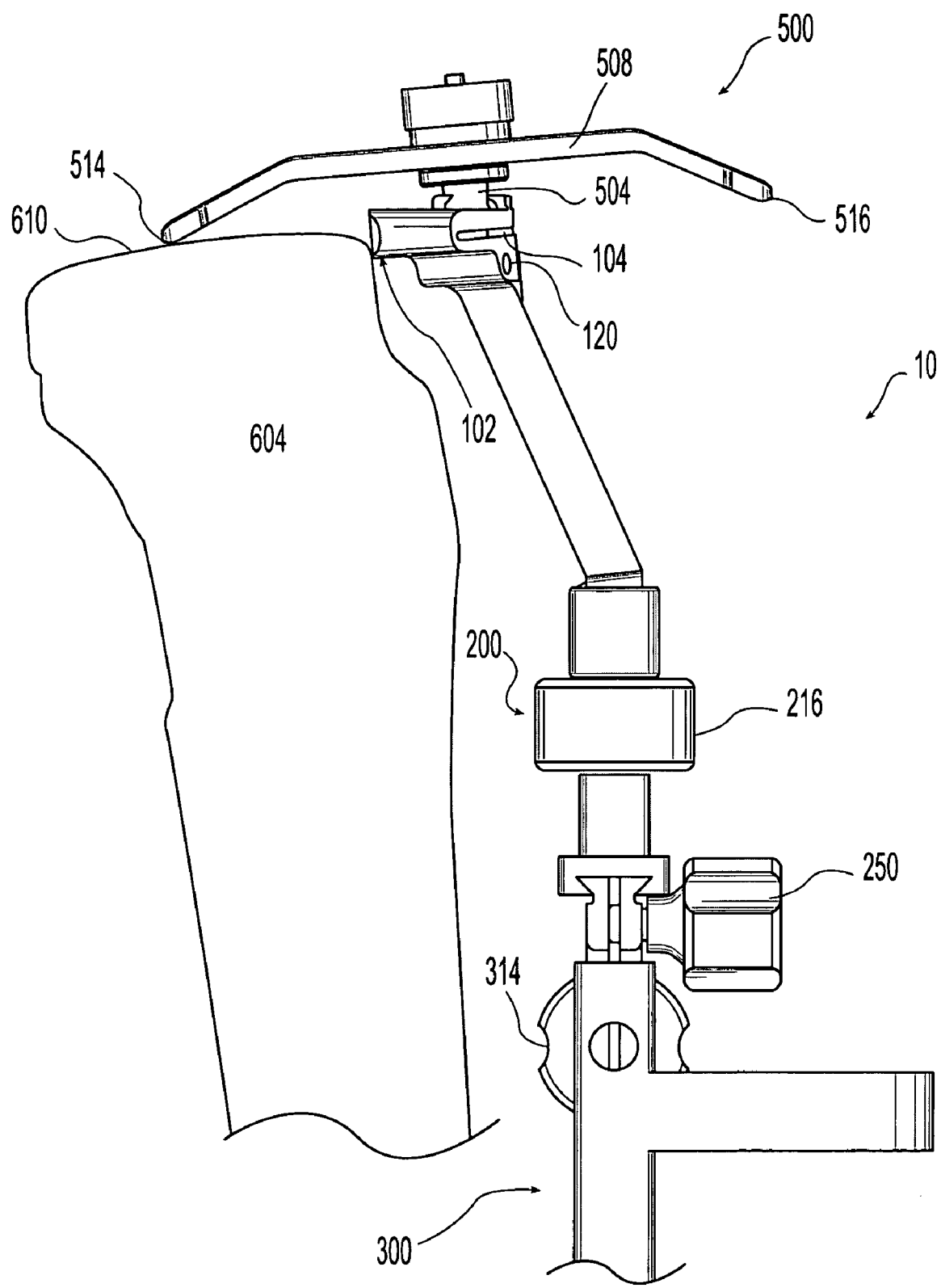
FIG. 6 is a side plan view of the upper portion of the resection guide of FIGS. 1-3 assembled with an optional illustrative tibial stylus and positioned on a bone.

An illustrative optional tibial depth setting stylus 500 is depicted in FIGS. 1 and 6. The stylus 500 includes a mounting base 502. A mounting post 504 extends distally from the mounting base 502 and includes a ball detent 505 for secure attachment of the stylus 500 to the tibial cut guide 100. A threaded post 506 extends proximally from the mounting base 502. A reference arm 508 includes a body 510 having a longitudinal slot 512 and opposite first and second reference tips 514, 516. The first and second tips 514, 516 are offset different distances distally from the body 510. The reference arm slot 512 receives the mounting base threaded post 506 and the reference arm 508 is secured to the mounting base 502 with a nut 518 and a washer 520. The stylus 500 is mounted on the tibial cut guide 100 by inserting the mounting post 504 into the axial bore 124 formed in the head 102 of the tibial cut guide 100. The ball detent 505 is biased outwardly by a captured spring (not shown) such that as the mounting post 504 is inserted, the ball detent 505 is forced back into the mounting post 504. As the ball detent 505 aligns with the cut slot 104, the ball detent 505 is biased into engagement with the slot 104 to secure the stylus 500 in a predetermined axial spacing from the cut slot 104. In this position, the first and second stylus tips 514, 516 are positioned at predetermined axial distances from the cut slot 104. By alternately positioning the first and second tips 514, 516 against the proximal tibial surface, the cut slot 104 may be positioned at two different predetermined cut depths to guide a cutter to remove different amounts of bone from the proximal tibial surface.

The above described instruments permit a variety of uses. They provide flexibility in mediolateral, anteroposterior, and proximal-distal positioning of the cut guides on the bone. They provide for referencing the proximal tibia and/or femur for establishing resection levels. They further provide for linked cutting of the tibia and femur or separate unlinked cutting of the tibia and femur.

The multiple mechanisms for mediolateral adjustment of the different portions of the instruments permit the instruments to be used in a midline position as in a total condylar knee surgery, in a medial position on a left or right knee in a unicondylar knee surgery, and in a lateral position on a left or right knee in a unicondylar knee surgery. The mediolateral adjustment at the ankle facilitates proper alignment of the distal portion of the instrument with the tibial axis. The mediolateral adjustment in the support assembly 200 permits alignment of the tibial cut guide 100 medially, centrally, or laterally on a left or right knee. Finally, the mediolateral adjustment between the femoral cut guide 400 and the tibial cut guide 100 permits the femoral cut guide 400 to be adjusted mediolaterally independently of the tibial cut guide 100 to optimize femoral cut guide 400 alignment on the femur.

The instrument incorporates both coarse and fine height adjustment to allow for rapid and accurate height settings. The support assembly 200 extension rod 236 may be slid proximal-distally within the ankle clamp assembly 300 for rapid height adjustment and gross positioning of the cut guides 100, 400. The screw mechanism controlled by the fine height adjustment knob 216 may then be used to fine tune the resection levels by positively dialing in the desired height.

The anteroposterior adjustment of the ankle clamp assembly 300 permits accurate positioning of the resection guide 10 parallel to the tibial axis to insure accurate anteroposterior resection slopes. These advantages and others will be apparent from the following description of illustrative surgical techniques.

In one exemplary surgical technique, the resection levels are set by referencing a femoral condyle 600 of a femur 602. This technique will be best understood by referring to FIGS. 4 and 5 showing the assembled adjustable resection guide 10 including the femoral cut guide 400. After exposing a portion of the knee joint the adjustable resection guide 10 is positioned adjacent the tibia 604. The arms 350 of the ankle clamp 340 are spread open and placed around the ankle 606. The coil springs 358 bias the arms to grip the ankle 606. The ankle clamp assembly 300 is aligned with the center of the ankle 606 by positioning the pointer 322 over the center of the ankle 606. The dovetail rail 332 is slid mediolaterally as necessary within the dovetail slot 344 of the ankle clamp 340. Once the assembly 300 is aligned, the MIL adjustment knob 370 is tightened to extend the end 376 of the shaft 372 and lock the mediolateral adjustment. Similarly, the anteroposterior position of the ankle clamp assembly 300 is adjusted so that the ankle clamp base 302 is parallel to the tibial axis 608. The A/P adjustment knob 362 is then tightened to lock the anteroposterior adjustment. With the coarse proximal-distal adjustment knob 314 loosened, the tibial cut guide 100 and support assembly 200 are adjusted to bring the tibial cut guide 100 into rough alignment with the approximate tibial resection level. This rough setting is locked by tightening the coarse adjustment knob 314. The mediolateral position of the tibial cut guide 100 and support assembly is adjusted by sliding the dovetail slot 234 of the support assembly 200 over the dovetail rail 244 of the extension rod 236. The mediolateral position is locked by tightening the M/L adjustment knob 250. The support assembly 200 is now secured to the tibia by driving fixation members through the fixation holes 230. Because of the proximity of the fixation holes 230 to the tibial cut guide head 102, the fixation members may be positioned within the incision made to expose the joint. The support assembly 200 and ankle clamp assembly 300 are now aligned and well fixed to the tibia 604 to provide a stable platform for subsequent instrument positioning. The femoral cut guide 400 is mounted on the tibial cut guide 100 by inserting the paddle 411 in the joint space between the femur 602 and tibia 604 and positioning the dovetail rail 418 adjacent the relieved portion 123 of the dovetail slot 122. The femoral cut guide 400 is translated posteriorly until the dovetail rail 418 engages the dovetail slot 122 opposite the relieved portion 123. The femoral cut guide 400 is translated mediolaterally to engage the dovetail slot 122 adjacent the relieved portion 123. With the femoral cut guide 400 mounted on the tibial cut guide 100, the fine height adjustment knob 216 is rotated to move the femoral cut guide 400 and tibial cut guide 100 as a single unit until the top surface 413 of the paddle 411 contacts the femoral condyle 600 with the leg in proper alignment. With the resection height now set, the surgeon has several surgical options.

A first option would be to fix both cut guides 100, 400 in place and cut both the femur 602 and the tibia 604 with the knee in extension. The tibial cut guide 100 is fixed in place by inserting fixation members through the fixation holes 120 in the tibial cut guide 100. The femoral cut guide 400 is adjusted mediolaterally by sliding the dovetail rail 418 in the dovetail slot 122 until the desired mediolateral position of the cut guide is reached. The femoral cut guide 400 is then fixed in place by inserting fixation members through the fixation holes 420 in the femoral cut guide 400. A cutter is guided through the tibial and femoral cut slots 104, 416 to remove portions of the tibia 604 and femur 602.

A second option would be to fix both cut guides 100, 400 and cut the femur 602 with the knee in extension. After the femur 602 has been cut, the femoral cut guide 400 is removed by removing the fixation members and sliding the femoral cut guide 400 until the dovetail rail 418 just clears the relieved portion 123 of the dovetail slot 122 and translating the femoral cut guide 400 anteriorly. The knee is then flexed to a convenient angle and the tibia 604 is cut. Both the first and second options are linked cuts in that the spacing between the cuts is established with the cut guides joined together in fixed predetermined spaced relationship.

A third option would be to cut either the tibia 604 or femur 602 at this stage and then use another technique to cut the other bone. For example, the tibial cut guide may be secured to the tibia 604 and the proximal tibial surface 610 may be resected. The adjustable resection guide 10 may then be removed and the femur 602 may be cut using another technique such as using spacer blocks as is known in the art. All three of these options rely on referencing the femoral condyle 600 to set the resection height for the femoral and/or tibial cuts.

In another exemplary surgical technique, the resection level is established by referencing the proximal tibial surface 610. This technique will be best understood by referring to FIG. 6 showing the assembled adjustable resection guide 10 including the tibial depth setting stylus 500. After exposing a portion of the knee joint the adjustable resection guide 10 is positioned adjacent the tibia 604 and the rough mediolateral, anteroposterior, and proximal-distal adjustments are made as described relative to the femoral referencing technique. However, rather than attaching the femoral cut guide 400, the tibial stylus 500 is attached to the tibial cut guide 100 by snapping the mounting post 504 into the bore 124 in the tibial cut guide 100. The desired amount of tibial resection is established by positioning the appropriate tip 514, 516 of the reference arm 508 over the proximal tibial surface 610. The fine height adjustment knob 216 is rotated to move the stylus 500 and tibial cut guide 100 as a single unit until one of the tips 514, 516 contacts the proximal tibial surface 610. The tibial cut guide 100 is now positioned to remove a predetermined amount of bone. The tibial cut guide 100 is secured to the tibia 604 by inserting fixation members through the fixation holes 120 and the proximal tibial surface 610 is resected by guiding a cutter through the tibial cut slot 104. The femoral cut guide 400 may be attached to the tibial cut guide 100 to set the femoral resection height. In this case, the cuts would be linked and based on tibial referencing. Alternatively, the femoral cut may be made using another technique such as using spacer guides.

It will be understood by those skilled in the art that the foregoing has described illustrative embodiments of the present invention and that variations may be made to these embodiments without departing from the spirit and scope of the invention defined by the appended claims.

What is claimed is:

1. An adjustable resection guide for guiding a cutter to cut bone adjacent a knee joint to prepare the bone to receive an implant, the knee joint including articulating ends of a tibia and a femur and having a medial aspect, a lateral aspect, an anterior aspect, and a posterior aspect, the tibia having a tibial axis extending from a proximal end near the knee joint to a distal end near an ankle joint, the guide comprising:
   an elongated base member having a proximal end, a distal end and a longitudinal axis therebetween, the base member being positionable adjacent the tibia with the longitudinal axis parallel to the tibial axis;
   a tibial cut guide having a guide surface for guiding a cutter to cut the tibia;
   a mediolateral adjustment mechanism interposed between the base member and the tibial cut guide, the mediolateral adjustment mechanism operable to adjust the tibial cut guide mediolaterally relative to the base member;
   a proximal-distal adjustment mechanism interposed between the base member and the tibial cut guide, the proximal-distal adjustment mechanism operable to adjust the tibial cut guide proximal-distally relative to the base member independently of the mediolateral adjustment, the mediolateral and proximal-distal adjustment mechanisms permitting the tibial cut guide to be positioned at a desired location adjacent the proximal tibia; and
   a modular femoral cut guide mountable to the tibial cut guide in relative mediolateral translating relationship, the femoral cut guide having a guide surface for guiding a cutter to cut the femur.

2. The resection guide of claim 1 wherein the proximal-distal adjustment mechanism comprises separate coarse adjustment and fine adjustment mechanisms.

3. The resection guide of claim 2 wherein the fine adjustment mechanism comprises male and female threaded members associated with the base member and tibial cut guide, the threaded members being threaded together such that turning one of the threaded members causes the tibial cut guide to translate relative to the base member in a direction parallel to the longitudinal axis of the base member.

4. The resection guide of claim 3 wherein the coarse adjustment mechanism comprises elongated members associated with the base member and tibial cut guide, the elongated members being telescoped together for relative translation in a direction parallel to the longitudinal axis of the base member.

5. The resection guide of claim 2 further comprising first fixation means for securing the resection guide to the tibia to fix the coarse proximal-distal adjustment and second fixation means for securing the tibial cut guide to the tibia to fix the fine proximal-distal adjustment.

6. The resection guide of claim 1 wherein the mediolateral adjustment mechanism comprises a dovetail slot and a dovetail rail mounted for relative mediolateral sliding and a clamping mechanism for clamping the dovetail rail within the dovetail slot at a desired mediolateral location.

7. The resection guide of claim 1 further comprising an ankle clamp coupled to the distal end of the base member in relative mediolateral translating relationship such that the distal end of the base member is adjustable mediolaterally relative to the ankle clamp, the ankle clamp including a locking mechanism for locking the distal end of the base member relative to the ankle clamp at a desired mediolateral location.

8. The resection guide of claim 1 wherein the guide surface of the femoral cut guide and the guide surface of the tibial cut guide are in fixed proximal-distal spacing while the femoral cut guide is adjusted mediolaterally relative to the tibial cut guide.

9. The resection guide of claim 8 wherein the femoral cut guide is mountable on the tibial cut guide via a dovetail rail and slot.

10. The resection guide of claim 1 wherein the tibial cut guide has a width and the femoral cut guide has a width, the femoral cut guide being mountable on the tibial cut guide with a two step motion wherein it is translatable in an anterior to posterior motion to initially engage the tibial cut guide while the tibial cut guide width is overlapping the femoral cut guide width and it is translatable in a mediolateral motion to fully engage the tibial cut guide such that the guides are engageable in a space narrower than their combined width.

11. The resection guide of claim 10 wherein the femoral cut guide is mountable on the tibial cut guide via a dovetail rail and slot, the dovetail rail extending mediolaterally a distance less than the width of the femoral cut guide and the dovetail slot extending only part way across the tibial cut guide to facilitate mounting the femoral cut guide on the tibial cut guide without requiring extreme relative mediolateral positioning of the cut guides, an anterior portion of the dovetail slot being relieved such that the femoral cut guide may be overlapped with the tibial cut guide and engaged by first translating the femoral cut guide posteriorly to engage a portion of the dovetail slot opposite the relieved portion and then translated mediolaterally to fully engage the dovetail slot.

12. The resection guide of claim 1 wherein the femoral cut guide further includes a paddle extending posteriorly from the cut guide, the paddle being engageable with the femur to establish the desired proximal-distal location of the tibial and femoral cut guides.

13. The resection guide of claim 12 wherein the paddle is removably mounted on the femoral cut guide.

14. The resection guide of claim 13 wherein the paddle is mounted in a slot spaced from the guide surface.

15. The resection guide of claim 1 further comprising a modular stylus mountable on the tibial cut guide in fixed proximal-distal relationship, the stylus being engageable with the tibia to establish a desired proximal-distal location of the tibial cut guide.

16. A method for guiding a cutter to cut bone adjacent a knee joint to prepare the bone to receive an implant, the knee joint including articulating ends of a tibia and a femur and having a medial aspect, a lateral aspect, an anterior aspect, and a posterior aspect, the tibia having a tibial axis extending from a proximal end near the knee joint to a distal end near an ankle joint, the method comprising:
providing a resection guide comprising an elongated base member having a longitudinal axis, the base member having a proximal end and a distal end, the base member being positionable adjacent the tibia with the longitudinal axis parallel to the tibial axis, a tibial cut guide having means for guiding a cutter to cut the tibia, and a stylus mountable on the tibial cut guide, the stylus having a reference surface for engaging the articulating end of the tibia, the tibial cut guide being mounted on the base member with a mediolateral adjustment mechanism interposed between the base member and the tibial cut guide, the mediolateral adjustment mechanism operable to adjust the tibial cut guide mediolaterally relative to the base member, and a proximal-distal adjustment mechanism interposed between the base member and the tibial cut guide, the proximal-distal adjustment mechanism operable to adjust the tibial cut guide proximal-distally relative to the base member, the proximal-distal adjustment mechanism comprising separate coarse adjustment and fine adjustment mechanisms;
positioning the base member adjacent the tibia;
mounting the stylus on the tibial cut guide;
inserting the stylus into the joint space between the tibia and femur;
adjusting the proximal-distal position of the tibial cut guide using the coarse and fine adjustment mechanisms until the stylus reference surface abuts the proximal tibial surface; and
adjusting the mediolateral position of the tibial cut guide relative to the base to position the tibial cut guide in a desired mediolateral position.

17. The method of claim 16 further comprising:
guiding a cutter to cut the tibia.

18. The method of claim 17 further comprising:
positioning the femoral and tibial cut guides simultaneously proximal-distally by moving the cut guides together as a unit and referencing the proximal tibial surface to set the resection level for both guides.

19. The method of claim 17 further comprising:
positioning the femoral and tibial cut guides simultaneously proximal-distally by moving the cut guides together as a unit and referencing the femur to set the resection level for both guides.

20. The method of claim 16 further comprising:
providing a femoral cut guide mountable on the tibial cut guide, the femoral cut guide comprising means for guiding a cutter to cut the femur;
mounting the femoral cut guide on the tibial cut guide such that the spacing between the tibial and femoral cuts is established with the cut guides connected together and the location of the cuts is referenced from the proximal tibial surface.

21. The method of claim 16 wherein the spacing between the tibial and femoral cuts established by the connected cut guides is equal to the total thickness of a joint implant to be inserted into the joint.

* * * * *

UNITED STATES PATENT AND TRADEMARK OFFICE
CERTIFICATE OF CORRECTION

PATENT NO.       : 7,641,661 B2
APPLICATION NO.  : 10/746385
DATED            : January 5, 2010
INVENTOR(S)      : Steffensmeier et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1224 days.

Signed and Sealed this

Sixteenth Day of November, 2010

David J. Kappos
*Director of the United States Patent and Trademark Office*